(12) United States Patent
Moreau et al.

(10) Patent No.: US 7,943,575 B2
(45) Date of Patent: May 17, 2011

(54) SUSTAINED RELEASE DRUG FORMULATIONS CONTAINING A CARRIER PEPTIDE

(75) Inventors: Jacques-Pierre Moreau, Upton, MA (US); Roland Cherif-Cheikh, Castelldefels (ES)

(73) Assignee: Ipsen Pharma S.A.S., Boulogne Billancourt (FR)

( * ) Notice: Subject to any disclaimer, the term of this patent is extended or adjusted under 35 U.S.C. 154(b) by 1144 days.

(21) Appl. No.: 10/506,263

(22) PCT Filed: Mar. 4, 2003

(86) PCT No.: PCT/US03/06676
§ 371 (c)(1),
(2), (4) Date: Jan. 31, 2005

(87) PCT Pub. No.: WO03/075887
PCT Pub. Date: Sep. 18, 2003

(65) Prior Publication Data
US 2005/0130900 A1 Jun. 16, 2005

Related U.S. Application Data

(60) Provisional application No. 60/361,592, filed on Mar. 4, 2002.

(51) Int. Cl.
*A61K 38/22* (2006.01)
(52) U.S. Cl. ................ 514/10.3; 514/11.2; 514/11.8
(58) Field of Classification Search .................. None
See application file for complete search history.

(56) References Cited

U.S. PATENT DOCUMENTS

| 5,252,565 A | 10/1993 | Peet et al. |
| 5,595,760 A * | 1/1997 | Cherif-Cheikh ............. 424/464 |
| 5,906,987 A | 5/1999 | Chwalisz et al. |

FOREIGN PATENT DOCUMENTS

| EP | 0 139 286 | 5/1985 |
| EP | 0 230 647 | 8/1987 |
| EP | 0 283 458 | 9/1988 |
| EP | 0 351 354 | 1/1990 |
| GB | 2 239 178 | 6/1991 |
| WO | 94/08623 | 4/1994 |
| WO | WO 94/08623 * | 4/1994 |
| WO | 98/03180 | 1/1998 |

OTHER PUBLICATIONS

Wan, J. et al., "Pseudo-zero order sustained release of a decapeptide from an injectable liquid crustal gel under physiologically relvant conditions," Pharmaceutical Research Supplement, Oct. 1, 1994, 11(10):S234, XP000562576 (Abstract).

* cited by examiner

*Primary Examiner* — Christopher R. Tate
*Assistant Examiner* — Roy Teller
(74) *Attorney, Agent, or Firm* — Hunton & Williams LLP

(57) ABSTRACT

The invention features a method of administering one or more therapeutic agents to a patient and delivering said agent or agents continuously over an extended period of time, said method comprising: obtaining a pharmaceutical composition including a peptide carrier, one or more therapeutic agents, and up to 30 percent, by weight, of a pharmaceutically acceptable, soluble, monomeric carrier; and parenterally administering said pharmaceutical composition to a subject by injection, wherein said composition automatically forms a gel after interaction with the patient's bodily fluids and releases said peptide carrier and said agent or agents continuously within the patient over an extended period.

36 Claims, No Drawings

SUSTAINED RELEASE DRUG FORMULATIONS CONTAINING A CARRIER PEPTIDE

The present application is the U.S. national phase of international application no. PCT/US03/06676, filed Mar. 4, 2003, which claims priority to U.S. provisional application No. 60/361,592, filed Mar. 4, 2002.

FIELD OF THE INVENTION

This invention relates to the sustained-release pharmaceutical compositions.

BACKGROUND OF THE INVENTION

Peptides are generally administered parenterally, e.g., by subcutaneous injection, since they are often degraded in the gastrointestinal tract. Many peptide treatments (e.g., insulin, LHRH, and somatostatin) require either the continuous or repeated administration of the peptide in the patient over an extended period of time. However, such continual injections cause both inconvenience and discomfort to the patient. Sustained-release formulations have been developed to deliver peptides over prolonged periods of time without the need for repeated injections. Solid polymeric microcapsules and matrixes, for example, utilizing biodegradable polylactic polymers, have been developed. See e.g., Hutchinson, U.S. Pat. No. 4,767,628 and Kent, et al., U.S. Pat. No. 4,675,189. Hydrogels have also been used as sustained-release formulations for peptides. These hydrogels comprise polymers such as poly-N-isopropyl acrylamide (NIPA), cellulose ether, hyaluronic acid, lecithin, and agarose to control the delivery. See, e.g., PCT Applications WO 94/08623.

Some peptides have been reported to form soluble aggregates or insoluble particulates once mixed into a solution. See, Eckhardt, et al., Pharm. Res., 8:1360 (1991). Others have studied the possibility of utilizing these peptide aggregates as sustained-release formulations. See European Patent Application 0510913 A2 (1992); and Wan, et al., Pharmaceutical Research, Vol. 11, 10 Suppl., abstracts P. S291 and P. S243 (1994). However, these aggregate sustained-release compositions require that the peptide be dissolved in saline or biologically compatible buffers, and then incubated until a liquid crystalline gel structure is formed.

Elsewhere it has been reported that certain soluble peptide salts can be formulated as sustained-release gel formulations without the addition of a biodegradable polymer or other carrier matrix to control the peptide's release profile. See Cherif-Cheikh, U.S. Pat. No. 5,595,760.

SUMMARY OF THE INVENTION

The present invention provides pharmaceutical compositions which automatically form a sustained-release gel within a patient without the need for any extemporaneous dissolution or incubation of the composition. The invention is based on the discovery that certain soluble peptides or salts thereof can themselves serve as sustained-release carriers to control not only the peptide's own release profile but also the release profile of one or more therapeutic agents. The new compositions formed with such "carrier peptides" automatically gel upon interaction with a patient's bodily fluids and then release both the peptide and the therapeutic agent or agents over an extended period of time. The new compositions thus reduce the volume, cost, and manufacturing time of known sustained-release polymer-based formulations.

In general, the invention features a method of administering a carrier peptide and a therapeutic agent or agents to a patient and delivering the carrier peptide and therapeutic agent or agents continuously over an extended period of time. The method comprises obtaining a solid pharmaceutical composition comprising a carrier peptide, i.e., a soluble, gelable peptide or salt of the peptide, and a therapeutic agent or agents and parenterally administering the solid composition to the patient by injection, e.g., intramuscular, subcutaneous, intradermal, or intraperitoneal, wherein the solid composition automatically forms a gel after interaction with the patient's bodily fluids and releases the carrier peptide and the therapeutic agent or agents continuously within the patient over an extended period.

One preferred group of therapeutic agents that may be included in a composition of the invention are dopamine agonists or antagonists, and their pharmaceutically acceptable salts. Preferred compounds from this group include, e.g., amantadine, bromocriptine, cabergoline, lisuride, mesulergine, pergolide, pramipexole, quinagolide, and ropinirole, and their pharmaceutically acceptable salts and analogs thereof. A particularly preferred compound from among this group is cabergoline and its pharmaceutically acceptable salts.

The compositions of the present invention advantageously allow for the administration of soluble and non-soluble therapeutic agents to a subject, e.g., over an extended period of time. Further, a composition of the present invention, e.g., as might contain a compound with poor solubility, gel or aggregation properties, may be manufactured so as to avoid undesirable solvents, temperatures, shear-stresses, and other undesirable conditions, i.e., conditions likely to destabilize molecules.

In one aspect the carrier peptide and the therapeutic agent or agents are released over a period of at least three days, preferably at least 7 days, more preferably at least 14 days, more preferably still at least 30 days.

In another aspect the carrier peptide itself is a therapeutic agent; i.e., is itself biologically active. In another embodiment the carrier peptide is itself essentially biologically inactive.

A by no means exhaustive nor limiting list of the types of peptides suitable for use as a carrier peptide in the invention include growth hormone (GH), growth hormone releasing peptide (GHRP), growth hormone releasing factor (GRF), epidermal growth factor, interferon, insulin, somatostatin, bombesin, calcitonin, calcitonin gene related peptide (CGRP), amylin, parathyroid hormone (PTH), parathyroid hormone related peptide (PTHrp), gastrin, gastrin releasing peptide (GRP), melanocyte stimulating hormone (MSH), adrenocorticotrophic hormone (ACTH), luteinizing hormone (LH), luteinizing hormone-releasing hormone (LHRH), cytokinases, sorbine, cholecystokinin (CCK), glucagon, glucagon-like peptide (GLP), gastrin, enkephalin, neuromedin, endothelin, substance P, neuropeptide Y (NPY), peptide YY (PYY), vasoactive intestinal peptide (VIP), pituitary adenylate cyclase activating polypeptide (PACAP), bradykinin, thyrotropin releasing hormone (TRH), beta-cell tropin (a fragment of ACTH), or biologically active or inactive analogs of any of the foregoing.

Preferred soluble, gelable carrier peptide salts according to the invention include salts of somatostatin and analogs such as SOMATULINE also known as lanreotide (Kinerton, Ltd., Dublin, Ireland; see, e.g., Johnson et al., Eur. J. Endocrinol. 130:229-34, 1994), salts of calcitonin and its analogs, salts of LHRH analogs such as the antagonist GANIRELIX, (GRX; see, e.g., Nestor et al., J. Med. Chem., 35(21):3942-3948, 1992), and salts of GH, GRF, PTH, PTHrp, and biologically active or inactive analogs thereof.

Examples of preferred salts are those with therapeutically acceptable organic acids (e.g., acetic, lactic, maleic, citric, malic, ascorbic, succinic, benzoic, methanesulfonic, or toluenesulfonic, and salts with inorganic acids such as the hydrohalic acids (e.g., hydrochloric acid), sulfuric acid, or phosphoric acid.

The gelable carrier peptides of the invention can be compounded with a pharmaceutically acceptable, monomeric, soluble carrier for ease of manufacture and/or administration. Examples of carriers include polyalcohols such as mannitol and sorbitol, sugars such as glucose and lactose, surfactants, organic solvents, and polysaccharides. Thus in another aspect the composition of the invention further comprises a pharmaceutically acceptable, soluble, monomeric carrier, e.g., mannitol, sorbitol, lactose, and the like, said monomeric carrier preferably being present in an amount of up to 30 percent by weight of the dry weight of said composition.

Solid compositions of the invention can be manufactured in the form of a cylinder with a diameter of less than 3 mm, and preferably less than 2 mm, for administration by standard trocar.

A semisolid suspension can also be used in the method of the invention. The terms "semisolid suspension" and "semisolid composition" are used interchangeably herein to refer to viscous, paste-like suspensions of a carrier peptide and a therapeutic agent or agents in a liquid solvent, such as sterilized water. A semisolid suspension according to the invention includes (1) a solid, soluble, carrier peptide, a therapeutic agent or agents, and up to 30 percent by weight of a pharmaceutically acceptable, soluble carrier; and (2) a solvent, e.g., an aqueous solvent like sterilized water, in an amount less than 50 percent, and preferably 20 or 10 percent, of the amount of solvent required to dissolve the peptide salt or any therapeutic agent or agents, to provide the semisolid consistency. The suspension may also be parenterally administered to the patient in one injection, and automatically forms a gel after interaction with the patient's bodily fluids.

The invention further features a sustained-release gel formed within a patient. The gel is made of (1) a pharmaceutical composition including a carrier peptide or carrier peptide salt, i.e., a soluble, gelable peptide or peptide salt, a therapeutic agent or agents, and up to 30 percent, by weight, of a pharmaceutically acceptable, soluble carrier, and (2) one or more bodily fluids of the patient, wherein the carrier peptide or peptide salt automatically forms the gel after interaction with the bodily fluids, and the gel releases the carrier peptide and the therapeutic agent or agents continuously within the patient over an extended period of time, preferably for at least three days after formation, more preferably for at least seven days, more preferably for at least 14 days, more preferably still for at least 30 days. The pharmaceutical composition that forms the gel can be a solid, or it can further include a solvent, e.g., sterilized water, in an amount less 50 percent of the amount of solvent required to dissolve the carrier peptide or peptide salt or the therapeutic agent or agents, and to provide the pharmaceutical composition with a semisolid consistency.

In addition, the invention features a solid, non-particulate, sustained-release pharmaceutical composition for parenteral administration to a patient. This composition-comprises (1) a soluble, gelable peptide or peptide salt (i.e., a carrier peptide or salt thereof), and a therapeutic agent or agents and (2) up to 30 percent, by weight, of a pharmaceutically acceptable, monomeric, soluble carrier, compounded into a solid cylindrical form, wherein the solid composition automatically forms a gel after interaction with the patient's bodily fluids, and releases the peptide continuously within the patient over an extended period time. Preferably the gel releases the carrier peptide and therapeutic agent or agents for at least three days after formation, more preferably at least seven days, more preferably at least 14 days, more preferably still at least 30 days.

The invention also features a semisolid, sustained-release pharmaceutical suspension for parenteral administration to a patient. This suspension consists essentially of (1) a soluble, gelable peptide salt (i.e., a carrier peptide or salt thereof), a therapeutic agent or agents, and up to 30 percent, by weight, of a pharmaceutically acceptable, soluble carrier; and (2) a solvent in an amount less than 50 percent, and preferably 20 or 10 percent, of the amount of solvent required to dissolve the carrier peptide or salt thereof or the therapeutic agent or agents and to provide the semisolid consistency of the suspension, wherein the semisolid suspension automatically forms a gel after interaction with the patient's bodily fluids and releases the carrier peptide and therapeutic agent or agents continuously within the patient over an extended period. Preferably the gel releases the carrier peptide and therapeutic agent or agents for at least three days after formation, more preferably at least seven days, more preferably at least 14 days, more preferably still at least 30 days.

In another aspect, the invention features a method of making a solid pharmaceutical composition by a) mixing a soluble, gelable peptide salt (i.e., a carrier peptide or salt thereof), a therapeutic agent or agents, and up to 30 percent, by weight, of a pharmaceutically acceptable, soluble carrier to form a mixture; b) compounding the mixture with a liquid vehicle to form a semisolid formulation; c) extruding the semisolid formulation to form an elongated filament; d) cutting the elongated filament into semisolid cylindrical rods; and e) drying the semisolid rods to form solid cylindrical rods. Preferably, the solid rods have a diameter of less than 2 or 3 mm.

The term "peptide" means a natural or synthetic molecule comprising two or more amino acids linked by the carboxyl group of one amino acid and the amino group of another. Thus, the term includes both polypeptides and proteins. A "soluble" peptide or peptide salt is one having a solubility of 0.1 mg/ml, and preferably 1.0 mg/ml, in water at a pH of 7.0 and a temperature of 25 degrees C.

As used herein, the term "carrier peptide" refers to a gelable peptide or gelable peptide salt, i.e., a peptide or peptide salt which will form a gel upon contact with bodily fluids. The carrier peptide is preferably soluble in water, as herein defined. Whether a peptide or peptide salt is gelable and will have the desired biological properties can be determined by testing the peptide or peptide salt in one or more of the in vitro and/or in vivo assays described below.

The term "analog" is used herein to cover any naturally occurring, recombinant, or synthetically synthesized peptide or non-peptide compound, or derivatives or fragments thereof, which compound may be biologically active or biologically inactive. By way of example in respect of, e.g., a naturally occurring peptide, the term would include, without limitation, peptides in which one or more of the N- or C-terminal group or side chain has been structurally modified, and/or in which one or more non-peptide or pseudopeptide bond has been included, and/or in which one or more amide nitrogen has had a substituent attached thereto.

The term "biologically active analog" is used herein to cover any analog that exhibits an agonist or antagonist effect relative to the corresponding unmodified or naturally occurring peptide or non-peptide compound.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference, each in its entirety. In addition, the materials, methods, and examples are illustrative only and not intended to be limiting.

Other features and advantages of the invention will be apparent from the detailed description, and from the claims.

DETAILED DESCRIPTION

The invention relates to pharmaceutical compositions, e.g., solid cylinders or semisolid suspensions, that automatically form sustained-release gels once administered to a patient. As is well known in the art, syringe and syringe-like devices may be used to administer semisolid suspensions while trocars and trocar-like devices may be used to administer solid compositions.

Each unit of the new compositions will contain at least the daily dose of the desired therapeutic agent or agents multiplied by the desired number of days of activity. After the composition automatically gels upon contact with bodily fluids, the carrier peptide and the therapeutic agent or agents are delivered from the gel according to a blood level profiles that are comparable to the blood level profiles of the carrier peptide and the therapeutic agent or agents when administered by continuous daily injection, by known sustained-release compositions, e.g., polymeric peptide formulations, or by an infusion pump operating under a steady mode of delivery.

Peptides Suitable for Pharmaceutical Compositions

Peptides or the salt forms thereof that can be used as carrier peptides in the compositions of the invention form a gel in bodily fluids, e.g., lymph or blood serum, when administered to a patient, and, once gelled, are capable of controlling the delivery of the carrier peptide and of a therapeutic agent or agents at a rate suitable for a therapeutic use of the carrier peptide and/or of the therapeutic agent or agents. For instance, gels using, e.g., somatostatin analogs such as SOMATULINE as the carrier peptide and DECAPEPTYL as the therapeutic agent are able to maintain a sustained release of therapeutic levels of SOMATULINE and DECAPEPTYL in the blood for one month or longer. See Example 1, below.

Peptides that are preferred for use as the carrier peptide in the new compositions include somatostatin, calcitonin, parathyroid hormone (PTH), parathyroid hormone related protein (PTHrP), soluble agonists or antagonists of LHRH, GRF, and other soluble analogs that have the agonist or antagonist effect of any of these peptides. Preferably, the carrier peptide comprises at least one hydrophobic residue, e.g., non-naturally occurring residues such as napthylalanine (NaI), norleucine (Nle), and halogen substituted phenylalanines, and naturally occurring residues such as Trp, Ile, Phe, Val, Leu, Met, Ala, Gly, or Cys, that allow the carrier peptide to better form a gel. Hydrophobicities of amino acids can be determined as discussed in Eisenberg, Ann. Rev. Biochem., 53:595-623 (1984).

The configuration of a carrier peptide of the composition is also preferably altered, e.g., by a D-amino acid to decrease enzymatic degradation, by a disulfide bridge to create a cyclic peptide, or by an internal amide bond between the side chains of two amino acid residues. These features of suitable carrier peptides are believed to allow or enhance the ability of the carrier peptide or peptide salt to automatically form a gel once administered to a patient.

The following publications disclose sequences of PTH peptides and analogs: John P. Bilezikian (ed.), The Parathyroids Basic and Clinical Concepts, pages 239-258 (Raven Press, N. H. 1994); Nissenson et al., "Structure & Function of the Receptor for Parathyroid Hormone and Parathyroid Hormone-Releasing Honnone," Receptor, 3:193-202 (1993); Bachem California 1993-1994 Catalog (Torrance, Calif.); and SIGMA.RTM., Peptides and Amino Acids 1994 Catalog (St. Louis, Mo.).

The following publications disclose sequences of PTHrP peptides and analogs: Yasuda, et al., J. Biol. Chem., 264: 7720-7725 (1989); and Burtis, W. J., Clin. Chem., 38(11): 2171-2183 (1992). More examples can be found in the following publications: PCT Application 94/01460 (1994); PCT Application 94/02510 (1994); PCT Application 93/20203 (1993); PCT Application 92/11286 (1992); PCT Application 93/06846 (1993); PCT Application 92/10515 (1992); PCT Application 92/00753 (1992); EP Application 477885 A2 (1992); EP Application 561412 A1 (1993); EP Application 451867 A1 (1991); German Application 4203040 A1 (1993); U.S. Pat. No. 4,771,124 (1988); U.S. Pat. No. 4,656,250 (1987); U.S. Pat. No. 5,229,489 (1993); and Bachem California 1993-94 Catalog, 30-34 (1993).

The following publications disclose sequences of somatostatin analogs: PCT Application WO 91/09056 (1991); EP Application 0 505 680 A1 (1992); EP Application 0 363 589 A2 (1990); EP Application 0 203 031 A2 (1986); U.S. Pat. No. 4,904,642 (1990); U.S. Pat. No. 4,871,717 (1989); U.S. Pat. No. 4,853,371 (1989); U.S. Pat. No. 4,725,577 (1988); U.S. Pat. No. 4,684,620 (1987); U.S. Pat. No. 4,650,787 (1987); U.S. Pat. No. 4,603,120 (1986); U.S. Pat. No. 4,585, 755 (1986); U.S. Pat. No. 4,522,813 (1985); U.S. Pat. No. 4,486,415 (1984); U.S. Pat. No. 4,485,101 (1984); U.S. Pat. No. 4,435,385 (1984); U.S. Pat. No. 4,395,403 (1983); U.S. Pat. No. 4,369,179 (1983); U.S. Pat. No. 4,360,516 (1982); U.S. Pat. No. 4,358,439 (1982); U.S. Pat. No. 4,328,214 (1982); U.S. Pat. No. 4,316,890 (1982); U.S. Pat. No. 4,310, 518 (1982); U.S. Pat. No. 4,291,022 (1981); U.S. Pat. No. 4,238,481 (1980); U.S. Pat. No. 4,235,886 (1980); U.S. Pat. No. 4,224,190 (1980); U.S. Pat. No. 4,211,693 (1980); U.S. Pat. No. 4,190,648 (1980); U.S. Pat. No. 4,146,612 (1979); U.S. Pat. No. 4,133,782 (1979); Van Binst et al., Peptide Res., 5:8 (1992); Prevost et al., Cancer Res., 52:893 (1992); and Bachem California 1993-1994 Catalog 94-95 (1993).

The following publications disclose sequences of GRF analogs: PCT Application WO 91/18998 (1991); PCT Application WO 92/18537 (1992); PCT Application WO 92/00095 (1992); PCT Application WO 91/03053 (1991); EP Application 314866 A2 (1989); EP Application 136475 B1 (1991); EP Application 320785 A2 (1989); U.S. Pat. No. 4,732,972 (1988); U.S. Pat. No. 4,627,312 (1986); EP Patent Application 511003 A1 (1992); and Bachem California 1993-1994 Catalog 64-65 (1993).

The following publications disclose sequences of LHRH analogs: U.S. Pat. Nos. 4,307,083; 4,292,313; 4,124,577; 4,111,923; 4,101,538; 4,101,537; 4,093,611; 4,087,419; 4,087,418; 4,087,417; 4,083,967; 4,062,835; 4,031,072; 4,031,070; 4,031,069; 3,824,227; 3,824,065; Rivier et al., J. Med. Chem., 29:1846 (1986); Ljungquist et al., Proc. Natl. Acad. Sci., USA, 85:8256 (1988); Coy et al., Amer. Clin. Res., 10:139 (1978); Sundaram et al., Life Sci., 28:83 (1981); Rivier et al., Life Sci., 23:869 (1978); Humphrey et al., J. Med. Chem., 21:120 (1978); and Bachem California 1993-1994 Catalog 67-68 (1993).

The following publications disclose sequences of calcitonin analogs: EP Application 464549 A1 (1992) and Bachem California 1993-1994 Catalog 28 (1993).

In vitro Assays for Suitable Peptide Salts

A simple in vitro assay can be used to determine the suitability of a given peptide or peptide salt for use as a carrier peptide in a composition of the present invention. The peptide or peptide salt, e.g., in the form of a powder or a suspension, is mixed with a clear bodily fluid, e.g., lymph, plasma, or serum, in a container. This container is heated to 37 degrees C., e.g., by a water or oil bath. A visual inspection is made to determine whether the peptide salt forms a gel.

An in vitro light diffraction assay can also be used to determine whether a peptide or peptide salt will be suitable for use in the present invention. The peptide or peptide salt, e.g., in the form of a powder, is mixed on a glass microscope slide with between 20 and 50 percent, by weight, of water. After being well mixed, e.g., after about 5 minutes, the slide is analyzed on an inverted microscope, such as the ZEISS AXIOVERT 100, using polarized light. If the polarized light is diffracted, as indicated by the presence of bright colors, the peptide salt has formed a gel, and is suitable for use in the present invention.

Another in vitro assay can be used to study the release characteristics of the solid and semisolid compositions of the invention. The MICROETTE transdermal diffusion cell (Hanson Research, Palo Alto, Calif.) is utilized in the assay as an autosampling system composed of, e.g., six thermostatic cells, a mechanical stirring device, and a sample collector.

When used to study the delivery profile of, e.g., solid SOMATULINE cylinders, the assay conditions for the autosampling system would be as follows: release medium=NaCl 0.9%, initial volume=7 ml, rod weight=1.6 to 1.8 mg., temperature=37 C., stirring rate=60 rpm, final stirring rate=400 rpm (for the last 15 min.), and replacement volume=481 mul. Samples can be taken at, e.g., 4, 10, 20, 40; 65, 90, 180 and 270 minutes.

The samples collected in the autosampler can be analyzed by high pressure liquid chromatography (HPLC) and quantified in a Hewlett Packard Series 1090 Liquid Chromatograph (Teknokroma, Barcelona, Spain) with automatic injector. A UV-VIS Diode Array detector may be used for the analysis. A NUCLEOSIL C-18 column, 25 cm×4.0 mm diameter, was used. Typical assay conditions for the HPLC are as follows: Component A=0.1% TFA in AcCN:Water (80:20); Component B=0.1% TFA in water; flow=0.9 ml/min.; injection volume=20 microliters; temperature=room temperature; detection=UV-280 nm; and acquisition time=20 minutes. The retention time of SOMATULINE was calculated to be 14 minutes. The gradient system used for the HPLC are depicted in Table I.

In vivo Assay of Sustained Peptide Release

Once a particular peptide or peptide salt is found to gel in an in vitro assay, e.g., an assay as described above, an in vivo assay can be used to determine the suitability of that peptide salt for use as a sustained-release carrier peptide of a therapeutic agent or agents in animals or humans. A blood level release profile for the carrier peptide and/or the therapeutic agent or agents can be determined by injecting the composition into an animal, e.g., a Sprague Dawley rat, a dog, etc., and testing blood samples taken at specific time intervals, e.g., hourly intervals over 1 to 5 days, or 12 or 24 hour intervals over 5 to 45 days, for the concentration of the peptide and/or therapeutic agent or agents. The suitability of a particular peptide gel, or a peptide/carrier gel, for therapeutic delivery of the carrier peptide and/or therapeutic agent or agents can thus be determined.

Generally, in such an assay animals are anaesthetized with pentobarbital (60 mg/kg i.p. for rats), and a jugular vein is cannulated for blood sampling. A test semisolid suspension or solid composition (or standard solution for comparison purposes), e.g., a SOMATULINE/DECAPEPTYL mixture, is injected subcutaneously at a specific dosage, e.g., 1.0, 3.0, or 6.0 mg/kg of SOMATULINE. After administration of the composition or solution, heparinized blood samples are obtained through the cannula at set time intervals, and plasma is separated after centrifugation. The amount of carrier peptide and/or therapeutic agent(s) in the plasma samples is/are determined by, e.g., a standard radioimmunoassay (RIA) technique that allows a direct measurement of the carrier peptide and/or therapeutic agent(s) without extraction from the rat plasma. The resulting data are plotted (e.g., blood concentration (ng/ml) vs. time) to establish a blood level release profile.

In addition, the presence of the carrier peptide and/or therapeutic agent(s) in the animal can be determined indirectly by assaying for any biological response of the animal. For example, if the carrier peptide or a therapeutic agent is a somatostatin analog, its effect, and thus presence, can be determined by assaying the inhibition of growth hormone release in response to GRF using standard assays. Such indirect methods of determining the presence of a biologically active carrier peptide or of a therapeutic agent can also be used in human patients.

When monitored for 1 to 3 days, this in vivo assay can be used to determine whether a particular carrier peptide will form a gel once administered in vivo that provides the desired sustained-release of the carrier peptide and/or one or more therapeutic agents. A carrier peptide is suitable for the present invention if it provides for sustained-release of the carrier peptide or a therapeutic agent over a desired period of time. Preferably the carrier peptide or a therapeutic agent is released at therapeutic levels for at least 3 days, more preferably for at least 7 days, more preferably at for least 14 days, more preferably still for at least 30 days.

This assay can also be used to determine the effectiveness of a particular peptide carrier or combination of peptide carrier and other carrier, and the necessary dosages, for use in a specific therapy for a particular animal, by comparing the blood level release profile to known dosage requirements for treatment of a particular disease using a particular therapeutic agent. Likewise, this assay can be used to estimate the expected effectiveness of a particular type and dosage of therapeutic agent for use in specific human therapies.

Carriers Suitable for Pharmaceutical Compositions

Although certain carrier peptides, e.g., salts of SOMATULINE, can be formulated into a solid composition without the need for any other carrier, the compositions of the invention also can be manufactured using carriers that are homogeneously compounded with the carrier peptide and therapeutic agent(s). The carrier should be water-soluble, monomeric, and directly eliminated by the body. Preferably, the carrier has a molecular weight of less than 1000 daltons. The carrier is chosen to give the composition its physical characteristics, but does not typically affect the sustained-release characteristics of the compositions. However, certain carriers can be used to decrease or increase both the release rate and the duration of delivery of the compositions. A non-exclusive list of such suitable carriers would include, without limitation, surfactants, e.g., TWEEN 80, polyalcohols, e.g., mannitol and sorbitol, monosaccharides, e.g., lactose and glucose, organic solvents, and polysaccharides.

Method of Preparing Solid Pharmaceutical Compositions

The manufacturing process of the invention avoids solubility problems of many peptides since there is no need to dissolve the peptide prior to injection. Another advantage of the solid compositions of the invention is their stability. The anhydrous, solid compositions of the invention avoid the problems of degradation, crystallization, aggregation, and coagulation associated with hydrated sustained-release formulations such as hydrogels.

One method for preparing a composition of the invention using a carrier in addition to the carrier peptide and loading the resulting drug composition for injection via a trocar needle is as follows.

The carrier, e.g., mannitol, is dissolved in a liquid manufacturing vehicle, e.g., water or an organic solvent. The resulting solution is mixed with the desired peptide carrier and therapeutic agent or agents to form a homogeneous semisolid mixture. If the final solid composition does not include a carrier, then the peptide carrier and therapeutic agent or agents are mixed solely with water or another liquid vehicle to form a semisolid mixture.

The semisolid mixture is then transferred to an extrusion chamber, e.g., a stainless syringe or a feeding extrusion area, with an plunger or a screw, and an extrusion nozzle with a 0.5 to 3.0 mm internal diameter. The mixture is extruded, cut into rods of a precise length, and collected. The resulting rods are thoroughly dried in a vacuum and preferably have a final diameter of 2 or 3 mm. Various known techniques can be used to move the non-solid mass of material through the orifice to produce the elongated rods with a desired cross-section once dried.

The manufacturing vehicle can be removed by evaporation, freeze-drying, or vacuum drying. The rods are then tested to determine the precise mass percentage of carrier peptide and therapeutic agent(s), i.e., dosage per unit length of cylinder. Five cylinders are taken from a batch, weighed, and then processed to remove the total amount of carrier peptide and therapeutic agent(s), e.g., by solubilization in an appropriate solvent such as 0.1% acetic acid in water. The amounts of extracted carrier peptide and therapeutic agent(s) are measured, e.g., using standard HPLC methodology as used in the in vitro assay described above.

Prior to use, the rods are also tested for uniformity by calculating their weight/length ratio. The lengths and weights of five cylinders are measured and the ratio of length to weight is calculated. Criteria are established regarding acceptable deviations from uniformity, e.g., the control is considered positive if the relative standard deviation (RSD) is less than 5%. This RSD equals $[SD_{length/weight/ratio}/Mean_{length/weight\ ratio}] \times 100$, so it is a measure of the uniformity of the length/weight ratio.

Once the rods have been accepted, the dosage is determined by length and weight measurement. Having already calculated the peptide concentration, the rods are cut into precise lengths corresponding to desired dosage units. The rods are tested once more prior to administration by weighing them on a balance. The rods are then ready to be loaded into hollow needles, e.g., of a trocar.

Trocar needles are loaded through the back end after the tip of the needle is sealed, e.g., with a cap. The back end of the needle preferably has a funnel shape, which makes it easy to insert the solid rods. A metallic plunger then pushes the rod out of the tip of the needle and into a patient.

In a preferred embodiment, the back end of the trocar needle is attached to a sterile stainless steel, plastic, or glass cylinder into which a semisolid composition is extruded, cut, and dried. The cylinder is situated such that when dried, the rod falls into the needle by gravity. The pre-loaded trocar needle is then ready to be connected with its metallic plunger system and its activating system to a standard trocar.

Method of Preparing Semisolid Suspensions and Freeze-Dried Compositions

Semisolid suspensions can be made using the same peptides and carriers used to make the solid compositions. However, compared to the solid compositions, the semisolid peptide suspensions are hydrated with between 10 and 90%, by weight, of an aqueous solvent (e.g., sterilized water) to form highly viscous or paste-like compositions. Preferably the water is added just prior to administration of the composition to a patient.

The semisolid suspensions can be manufactured by the same process as described above for solid compositions, i.e., by extrusion, but without the final vehicle removal step. The semisolid extruded rods can be directly injected into a patient with a syringe-like device, e.g., as described below. Alternatively, the dried, solid rods can be rehydrated to form a semisolid suspension prior to injection.

Semisolid compositions can also be manufactured by a freeze-drying process which simplifies the unit dosage control and allows simple sterilization before the composition is loaded into a needle. In this process, the carrier peptide and therapeutic agent, with or without an additional carrier, is first dissolved in water. The resulting solution is sterilized by passage through a 0.22 micron filter under pressure, e.g., using a syringe with a plunger. Once filtered, the solution must be handled under sterile conditions. Volume is precisely controlled, e.g., with a micropipette, and the sterile solution is filled into a sealed syringe cylinder. The liquid in the cylinder is then freeze-dried. The resulting lyophilized solid volume is compacted, e.g., using a plunger, in the syringe under vacuum.

The syringe containing the compacted, sterile solid is then packaged under vacuum. The solid composition will remain stable in this condition for extended periods of time without need of refrigeration or other special storage conditions. The solid composition is hydrated with water just prior to administration, e.g., using the two-part device described in U.S. Pat. No. 5,595,760, which contains the requisite volume of sterile water in a separate syringe-like cylinder. The freeze-dried solid is rehydrated to form a viscous, semisolid suspension that can then be injected into a patient.

A solution of the composition of the invention is undesirable, because such a solution, once injected, will disperse and not form the sustained-release gel of the invention. Thus, the amount of water is carefully selected to be less than that required to dissolve a specific amount of any active component of the composition. For example, at 25 degrees C., pH 7.0, 1.0 ml or less of water is required when mixed with 26 mg of the acetate salt of SOMATULINE to avoid the formation of a solution. By using an amount of water that is less than 50 percent, and preferably less than 20 or 10 percent, of the amount of water required to dissolve the carrier peptide or any therapeutic agent, a semisolid or paste-like suspension, rather than a solution, is ensured.

In a preferred embodiment, a needle is attached to the syringe cylinder with a funnel shaped connector. The funnel shaped connector can be part of the needle or part of the syringe. The needle can be fixed on the syringe or attached to the syringe just prior to use. The needle is adapted, in length and outer diameter, to the injection route, e.g., intramuscularly, intradermally or subcutaneously. The inside surface of the needle is preferably smooth to aid the injection of the semisolid composition.

The syringe preferably has a plunger of small diameter (1 to 5 mm) so that the small volume of semisolid composition (10 microliters to 300 microliters) will represent a significant length in the syringe barrel. This allows more accurate visualization and dosage measurement.

COMPOSITION EXAMPLES

Compositions of the present invention may be prepared using techniques well-known in the art of pharmaceutical formulation. In general compositions of the invention are prepared by mixing a carrier peptide with one or more therapeutic agents and, if desired, one or more pharmaceutically acceptable, monomeric, soluble carriers, adding an appropriate solvent thereto, and then mixing until a uniform consistency is achieved. One convenient method to prepare a composition of the invention involves the steps of mixing
(1) weighing of the product (Xg A+Yg B);
(2) Putting both dry powder into a reservoir preferentially a stainless steal syringe and making a physical mixture, e.g., using a TURBULA® shaker mixer;
(3) reducing the volume to the one of the future semisolid mixture (i.e. moving the plunger to a position where the dead volume will correspond then to the water contain of the semisolid);
(4) putting the powder mixture under vacuum with a vacuum pump (tube-connection through a filter);
(5) connecting with a valve this mixture to a liquid reservoir (other stainless steal syringe) with water or aqueous medium; and
(6) connecting both reservoirs and performing the mixture by push-pull on syringes' plungers rods. When the mixture is ready, it can be loaded into syringes the way we make it with the one component semisolid.

Example 1

SOMATULINE/DECAPEPTYL Composition 87.5 mg of DECAPEPTYL-acetate was dissolved in 2.6 ml water and placed in a first 5 ml syringe. 1.0 g of SOMATULINE was placed in a second 5 ml syringe and the second syringe placed under vacuum. The two syringes were connected via a valve and Millipore filter, the valve was opened, and the DECAPEPTYL solution allowed to flow into the evacuated SOMATULINE syringe. 10 transfers of the resultant solution was made between the two syringes via alternate depression of their respective plungers producing a homogeneous, semi-solid mixture.

Example 2

SOMATULINE/CABERGOLINE Composition 1.0 g. SOMATULINE and 0.1 g CABERGOLINE are added to a 5.0 ml syringe. The two powders are dry-mixed wit a spatula and put under vacuum, e.g., using a vacuum pump. The mixed powder is connected via a valve to another 5 ml syringe containing 2.6 ml water. The valve is opened and the water is mixed with powder through the valve. 10 transfers of the resultant solution are made between the two syringes via alternate depression of their respective plungers to produce a homogeneous, semi-solid mixture. The semisolid is then loaded into 0.3 ml insulin syringes at doses of 0.225 ml.

IN VIVO EXAMPLE 0.15 ml of the foregoing semisolid mixture from Example 1 was loaded into a 0.3 ml insulin syringe and was injected into beagle dogs. Blood samples were collected and standard radioimmunoassay (RIA) analysis was performed thereon. The results are depicted in Table 1, below.

TABLE 1

Pharmacokinetic Profile of a SOMATULINE/DECAPEPTYL Composition

| DECAPEPTYL (ng/ml) | SOMATULINE (ng/ml) | TIME (days) |
|---|---|---|
| 0.00 | 0.02 | 0.00 |
| 2.66 | 3.91 | 0.01 |
| 6.04 | 7.29 | 0.02 |
| 9.97 | 9.34 | 0.04 |
| 16.45 | 12.60 | 0.08 |
| 17.28 | 17.33 | 0.17 |
| 21.24 | 19.46 | 0.25 |
| 23.07 | 17.83 | 0.38 |
| 8.11 | 11.37 | 1.00 |
| 3.97 | 9.51 | 1.99 |
| 3.16 | 7.77 | 3.02 |
| 1.35 | 6.63 | 6.04 |
| 0.94 | 5.99 | 8.04 |
| 0.50 | 4.88 | 10.06 |
| 0.42 | 3.14 | 13.04 |
| 0.32 | 2.54 | 15.05 |
| 0.24 | 1.85 | 17.02 |
| 0.19 | 1.46 | 20.14 |
| 0.13 | 1.30 | 22.04 |
| 0.11 | 1.11 | 24.06 |
| 0.07 | 0.65 | 27.12 |
|  | 0.52 | 29.11 |
|  | 0.52 | 31.05 |
|  | 0.50 | 34.11 |
|  | 0.45 | 36.12 |
|  | 0.34 | 38.03 |
|  | 0.27 | 41.03 |
|  | 0.17 | 45.10 |
|  | 0.14 | 48.36 |
|  | 0.15 | 49.99 |
|  | 0.21 | 52.01 |
|  | 0.14 | 57.04 |
|  | 0.27 | 59.08 |
|  | 0.21 | 64.02 |
|  | 0.20 | 66.02 |
|  | 0.16 | 69.01 |
|  | 0.15 | 71.15 |

As will be readily appreciated, the peak concentration and duration of release may be easily modulated by varying the relative amounts of peptide carrier and therapeutic agent, as well as the total amount of composition given.

A similar study may be performed, e.g., for the composition of Example 2. Alternatively, the pharmacokinetic profile of the therapeutic agent may be approximated by assaying only the pharmacokinetic profile of SOMATULINE of the composition, the Cabergoline release expected to be proportional thereto.

Other Embodiments

It is to be understood that while the invention has been described in conjunction with the detailed description thereof, that the foregoing description is intended to illustrate and not limit the scope of the invention in any way. Other aspects, advantages, and modifications are within the claims.

What is claimed is:
1. A sustained-release pharmaceutical composition for parenteral administration to a subject, comprising a carrier peptide comprising somatostatin or lanreotide, or a salt thereof, and one or more therapeutic agent(s) comprising a biologically active LHRH analogue, a dopamine agonist or a dopamine antagonist, or a salts thereof, wherein said compo- sition automatically forms a gel after interaction with said subject's bodily fluids, said gel releasing both the carrier peptide and the therapeutic agent(s) continuously within the patient over an extended period of time.

2. A semisolid, sustained-release pharmaceutical suspension for parenteral administration to a subject, said suspension consisting essentially of: (1) a carrier peptide comprising somatostatin or lanreotide, or a salt thereof, one or more other therapeutic agent(s) and up to 30 percent, by weight, of a pharmaceutically acceptable, soluble, monomeric carrier, wherein said carrier peptide and said monomeric carrier are soluble in aqueous solvents; and (2) an aqueous solvent in an amount less than 50 percent of the amount of solvent required to dissolve said carrier peptide, wherein said semisolid suspension automatically forms a gel after interaction with the subject's bodily fluids, said gel releasing both the carrier peptide and the other therapeutic agent(s) continuously within the patient over an extended period time.

3. The suspension of claim 2, wherein said amount of solvent is less than 10 percent of the amount of solvent required to dissolve said carrier peptide.

4. A sustained-release gel, said gel comprising a carrier peptide comprising somatostatin or lanreotide, or a salt thereof, one or more therapeutic agent(s) comprising a biologically active LHRH analogue, a dopamine agonist, or a dopamine antagonist, or a salts thereof, wherein the gel releases both the carrier peptide and the therapeutic agent(s) continuously within a patient over an extended period time.

5. The gel of claim 4, wherein said gel is in the form of a pharmaceutical solid.

6. The gel of claim 5, wherein said pharmaceutical further comprises a solvent in an amount less than 50 percent of the amount of solvent required to dissolve said carrier peptide and to provide said pharmaceutical composition with a semisolid consistency.

7. A method of administering a carrier peptide and one or more other therapeutic agent(s) to a subject and delivering both the carrier peptide and the other therapeutic agent(s) continuously over an extended period of time, said method comprising:
   obtaining a solid pharmaceutical composition consisting essentially of the carrier peptide, wherein the carrier peptide is selected from somatostatin or lanreotide, or a salt thereof, the other therapeutic agent(s), and up to 30 percent, by weight, of a pharmaceutically acceptable, soluble, monomeric carrier, wherein said carrier peptide and said monomeric carrier are soluble in aqueous liquids, and
   parenterally administering said solid composition to the patient, wherein said solid composition automatically forms a gel after interaction with the subject's bodily fluids, said gel releasing both the carrier peptide and the other therapeutic agent(s) continuously within the patient over an extended period of time.

8. The method of claim 7, wherein said solid composition is administered intramuscularly, subcutaneously, or intradermally.

9. The method of claim 7, wherein said solid composition comprises no monomeric carrier.

10. The method of claim 7, wherein the monomeric carrier is mannitol, sorbitol, or lactose.

11. The method of claim 7, wherein said solid composition is in the form of a cylinder with a diameter of less than 3 mm.

12. The method of claim 7, wherein said gel releases said carrier peptide continuously over a period of at least 14 days.

13. The method of claim 7, wherein said gel releases said other therapeutic agent(s) continuously over a period of at least 14 days.

14. A method of administering a carrier peptide and one or more therapeutic agent(s) to a subject continuously over an extended period of time, said method comprising obtaining a semisolid suspension comprising (1) the carrier peptide, wherein the carrier peptide comprises somatostatin or lanreotide, or a salt thereof, and the therapeutic agent(s), comprising a biologically active LHRH analog, a dopamine agonist, and a dopamine antagonist, or a salts thereof, and (2) an aqueous solvent in an amount less than 50 percent of the amount of solvent required to dissolve said peptide carrier and to provide said semisolid consistency; and
   parenterally administering said semisolid suspension to the subject, wherein said semisolid suspension automatically forms a gel after interaction with the subject's bodily fluids, said gel releasing both the peptide carrier and the therapeutic agent(s) continuously within the patient over an extended period of time.

15. The method of claim 14, wherein said amount of solvent is less than 10 percent of the amount of solvent required to dissolve said peptide carrier.

16. The composition of claim 1, comprising a therapeutic agent(s) comprising a dopamine agonist or antagonist, or a pharmaceutically acceptable salt thereof.

17. The composition of claim 16 wherein said dopamine agonist is amantadine, bromocriptine, cabergoline, lisuride, mesulergine, pergolide, pramipexole, quinagolide, or ropinirole, or a pharmaceutically acceptable salt or analog thereof.

18. The composition of claim 17 wherein said dopamine agonist is cabergoline, or a pharmaceutically acceptable salt thereof.

19. The suspension of claim 2 or 3, wherein the therapeutic agent(s) comprise a dopamine agonist or antagonist, or a pharmaceutically acceptable salt thereof.

20. The suspension of claim 19 wherein said dopamine agonist is amantadine, bromocriptine, cabergoline, lisuride, mesulergine, pergolide, pramipexole, quinagolide, or ropinirole, or a pharmaceutically acceptable salt or analog thereof.

21. The suspension of claim 20, wherein said dopamine agonist is cabergoline, or a pharmaceutically acceptable salt thereof.

22. The sustained-release gel of claim 4, 5, or 6, wherein the therapeutic agent(s) comprise a dopamine agonist or antagonist, or a pharmaceutically acceptable salt thereof.

23. The sustained-release gel of claim 22 wherein said dopamine agonist is amantadine, bromocriptine, cabergoline, lisuride, mesulergine, pergolide, pramipexole, quinagolide, or ropinirole, or a pharmaceutically acceptable salt or analog thereof.

24. The sustained-release gel of claim 23 wherein said dopamine agonist is cabergoline, or a pharmaceutically acceptable salt thereof.

25. The method of any one of claim 7, 8, or 9-13, wherein the therapeutic agent(s) comprise a dopamine agonist or antagonist, or a pharmaceutically acceptable salt thereof.

26. The method of claim 25 wherein said dopamine agonist is amantadine, bromocriptine, cabergoline, lisuride, mesulergine, pergolide, pramipexole, quinagolide, or ropinirole, or a pharmaceutically acceptable salt or analog thereof.

27. The method of claim 26 wherein said dopamine agonist is cabergoline, or a pharmaceutically acceptable salt thereof.

28. The method of any one of claim 14 or 15 wherein wherein the therapeutic agent(s) comprise a dopamine agonist or antagonist, or a pharmaceutically acceptable salt thereof.

29. The method of claim 28 wherein said dopamine agonist is amantadine, bromocriptine, cabergoline, lisuride, mesulergine, pergolide, pramipexole, quinagolide, or ropinirole, or a pharmaceutically acceptable salt or analog thereof.

30. The method of claim 29 wherein said dopamine agonist is cabergoline, or a pharmaceutically acceptable salt thereof.

31. A sustained-release pharmaceutical composition for parenteral administration to a subject, comprising a carrier peptide comprising somatostatin or lanreotide, or a salt thereof, and one or more therapeutic agent(s), wherein said composition automatically forms a gel after interaction with said subject's bodily fluids, said gel releasing both the carrier peptide and the therapeutic agent(s) continuously within the patient over an extended period of time wherein said composition further comprises a pharmaceutically acceptable, soluble, monomeric carrier, wherein said carrier peptide and said monomeric carrier are soluble in aqueous solvents, and the monomeric carrier is present in an amount of up to 30 percent, by weight, of the composition.

32. The composition of claim 31, wherein said composition further comprises an aqueous solvent, wherein the aqueous solvent is present in an amount less than 50 percent of the amount of solvent required to dissolve the carrier peptide.

33. A method of administering a carrier peptide and one or more therapeutic agent(s) to a subject continuously over an extended period of time, said method comprising obtaining a semisolid suspension comprising (1) the carrier peptide, comprising from somatostatin or lanreotide, or a salt thereof, and the therapeutic agent(s), and (2) an aqueous solvent in an amount less than 50 percent of the amount of solvent required to dissolve said peptide carrier and to provide said semisolid consistency; and parenterally administering said semisolid suspension to the subject, wherein said semisolid suspension automatically forms a gel after interaction with the subject's bodily fluids, said gel releasing both the peptide carrier and the therapeutic agent(s) continuously within the patient over an extended period of time wherein said semisolid suspension further comprises a pharmaceutically acceptable, soluble, monomeric carrier, wherein said carrier peptide and said monomeric carrier are soluble in aqueous solvents, and the monomeric carrier is present in an amount of up to 30 percent, by weight, of the composition.

34. The method of claim 14, wherein said composition further comprises an aqueous solvent, wherein the aqueous solvent is present in an amount less than 50 percent of the amount of solvent required to dissolve the carrier peptide.

35. The composition of claim 1, wherein the composition comprises triptoreline acetate as the therapeutic agent.

36. The composition of claim 1, wherein the composition comprises carbergoline as the therapeutic agent.

\* \* \* \* \*